(12) United States Patent
Walker et al.

(10) Patent No.: US 8,196,453 B2
(45) Date of Patent: Jun. 12, 2012

(54) SENSOR FOR DETECTING SURFACE CRACKS IN AN ARTICLE

(75) Inventors: Lawrence John Walker, Karrinyup (AU); Nigel Laxton, Mt. Hawthorn (AU); Andrew Petrow, Waterford (AU); Duncan Barton, Woodlands (AU); Peter Hughes, Woodvale (AU)

(73) Assignee: Structural Monitoring Systems Ltd., Osborne Park, Western Australia (AU)

( * ) Notice: Subject to any disclaimer, the term of this patent is extended or adjusted under 35 U.S.C. 154(b) by 576 days.

(21) Appl. No.: 12/296,207

(22) PCT Filed: Apr. 5, 2007

(86) PCT No.: PCT/AU2007/000458
§ 371 (c)(1),
(2), (4) Date: Sep. 14, 2009

(87) PCT Pub. No.: WO2007/115363
PCT Pub. Date: Oct. 18, 2007

(65) Prior Publication Data
US 2010/0058838 A1     Mar. 11, 2010

(30) Foreign Application Priority Data
Apr. 7, 2006   (AU) ................................ 2006901823

(51) Int. Cl.
*G01M 3/02*     (2006.01)
(52) U.S. Cl. .......................................................... 73/37
(58) Field of Classification Search ............... 73/37, 104
See application file for complete search history.

(56) References Cited

U.S. PATENT DOCUMENTS

| 4,104,906 | A | 8/1978 | Oertle |
| 4,979,390 | A | 12/1990 | Schupack et al. |
| 5,770,794 | A | 6/1998 | Davey |
| 6,715,365 | B2 * | 4/2004 | Davey ............................ 73/799 |
| 2002/0029614 | A1 | 3/2002 | Davey |

FOREIGN PATENT DOCUMENTS
WO     01/98746 A1     12/2001

OTHER PUBLICATIONS

International Search Report for parent application PCT/AU2007/000458, having a mailing date of May 25, 2007.

* cited by examiner

*Primary Examiner* — Hezron E Williams
*Assistant Examiner* — Nathaniel Kolb
(74) *Attorney, Agent, or Firm* — Andrus, Sceales, Starke & Sawall, LLP

(57) ABSTRACT

A laminated sensor comprises a base stratum and a terminal stratum. The base stratum has a first surface that is affixed to a surface of a structure to be monitored. The terminal stratum is affixed to the opposite second surface of the base stratum. A connector is attached to the terminal stratum. The base stratum is provided with first and second channels and that are cut through the thickness of the base stratum. The terminal stratum is provided with holes that extend through the thickness of the terminal stratum. A first pair of the holes are positioned to register with the first channel, while a second pair of the holes are positioned to register with the second channel. A first conduit is formed by the first channel and the holes; while a second conduit is formed by the second channel and the holes. The connector connects with tubes to provide fluid communication between the conduits and a differential pressure monitoring system.

46 Claims, 12 Drawing Sheets

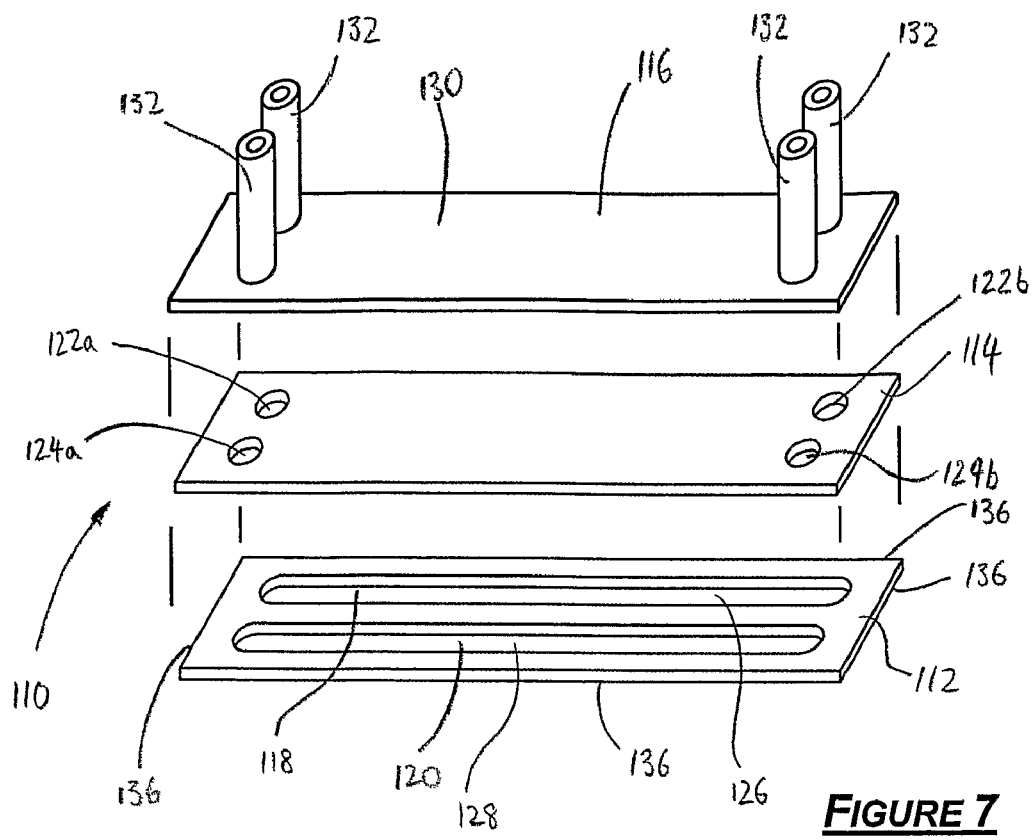
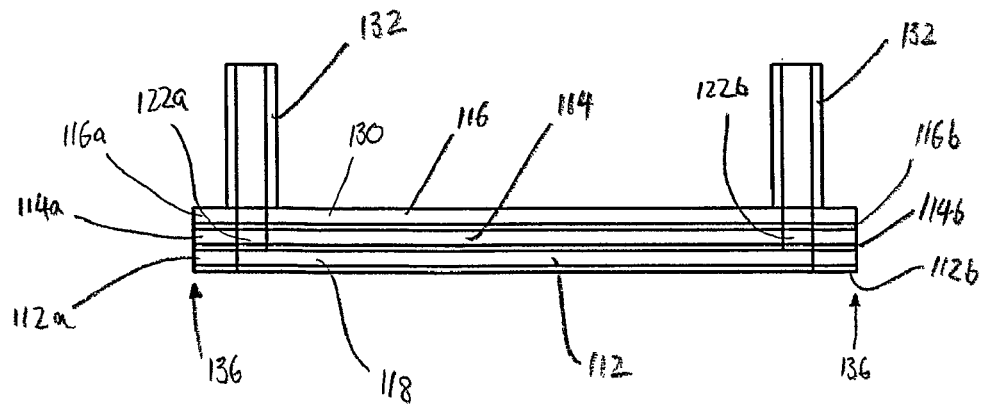
FIGURE 7
FIGURE 8

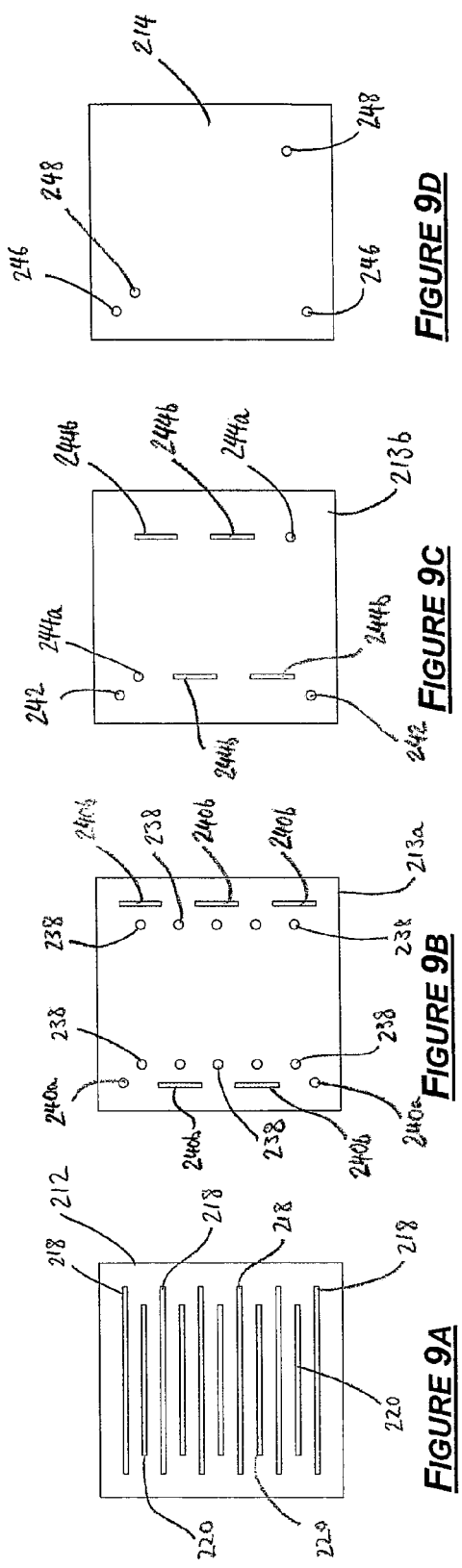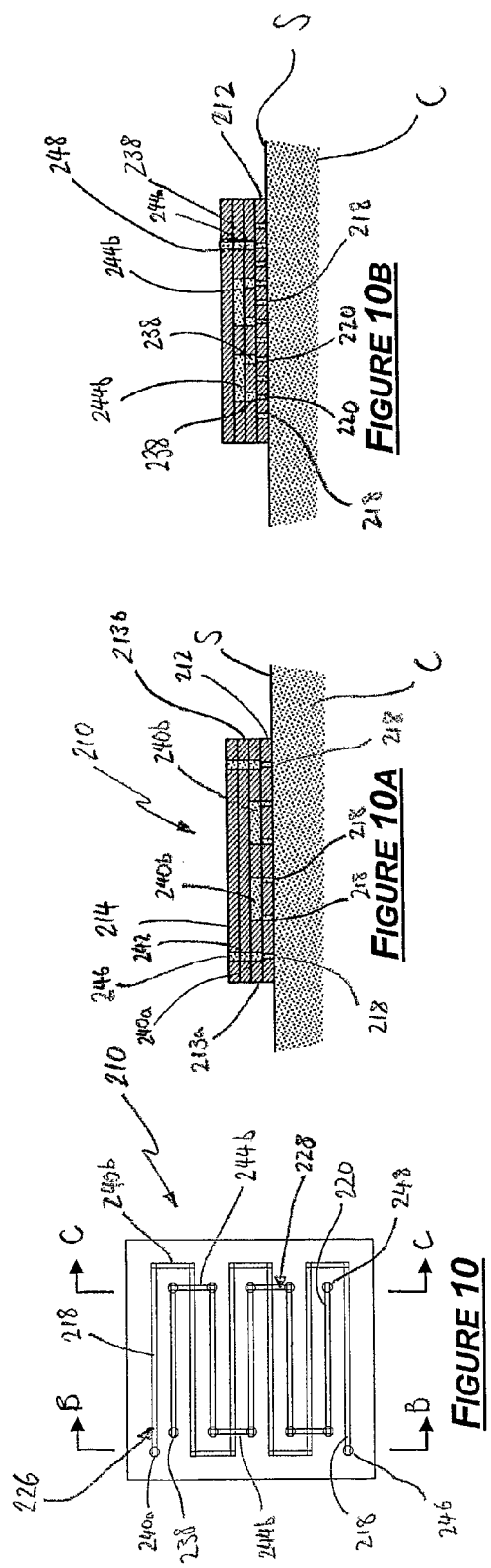

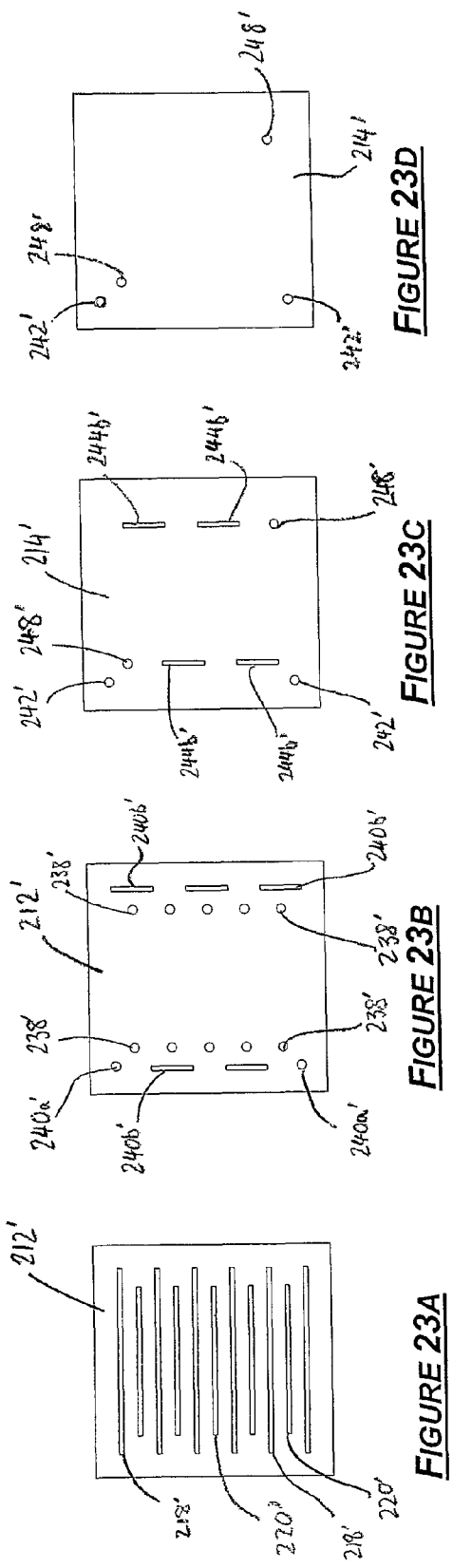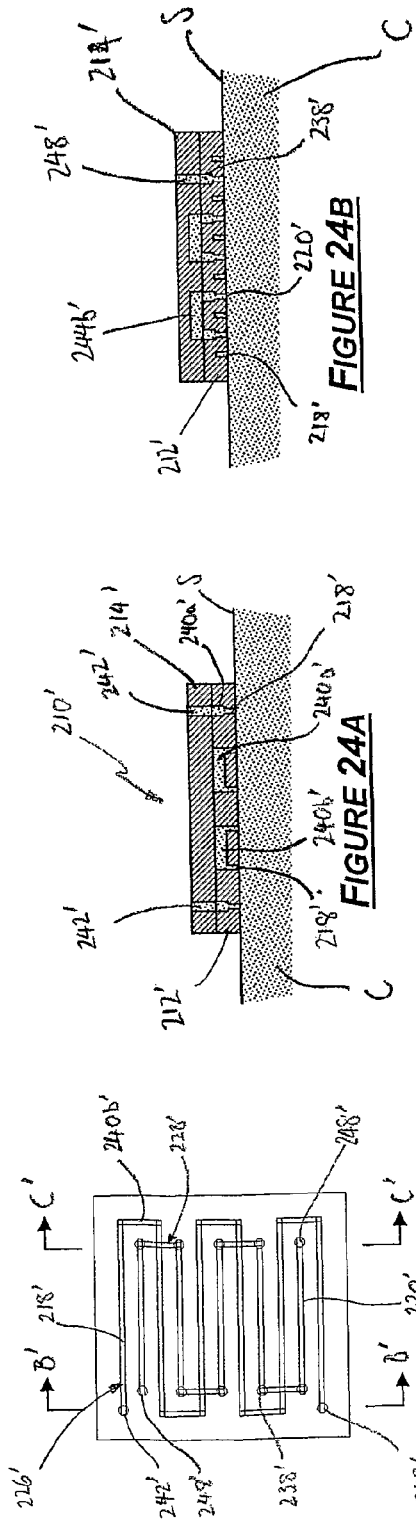

SENSOR FOR DETECTING SURFACE CRACKS IN AN ARTICLE

CROSS-REFERENCE TO RELATED APPLICATIONS

This application is the U.S. national stage application of International Application No. PCT/AU2007/000458, filed Apr. 5, 2007, which International application was published on Oct. 18, 2007, as International Publication No. WO 2007/115363 A1 in the English language, which application is incorporated herein by reference. The International application claims priority of Australian Patent Application No. 2006901823, filed Apr. 7, 2006, which application is incorporated herein by reference.

FIELD OF THE INVENTION

The present invention relates to a sensor for detecting surface cracks in an article.

BACKGROUND OF THE INVENTION

A number of techniques exist for Non-Destructive Testing (NDT) of components for the presence of surface cracks. Some observation based techniques employ, for example, ultrasonic or radiographic inspection. Other techniques, such as eddy current methods, use material response characteristics to indicate the presence of flaws.

It is generally accepted that NDT methods that can be performed in situ are preferable as this can avoid the need to take the equipment "off line", thus avoiding down time of the equipment and component to be tested. One in situ method for testing for the presence of surface cracks in a component involves establishing a pressure differential between at least two enclosed regions on the surface of the component. A surface crack of sufficient size that extends between two regions of differential pressure will cause a flow of air through the crack from the region of higher pressure towards the region of lower pressure. Monitoring for such a flow of air can be indicative of the presence of a surface flaw.

International Patent Application No. PCT/AU01/00504 (filed by the present applicant) discloses a system for monitoring the integrity of a structure. The system includes a sensor pad having a surface, which is sealed onto the surface of the structure to monitor for the presence of a flaw (such as a crack) within the structure and opening onto the surface.

SUMMARY OF THE INVENTION

According to one aspect of the present invention there is provided a sensor for detecting the presence of a surface crack in a component, the sensor comprising:
  a base stratum that, in use, is affixed to the surface of the component, the base stratum having one or more channels that each extend through the thickness of the base stratum, and
  a terminal stratum that is affixed to the base stratum, the terminal stratum having at least one hole that each extends through the thickness of the terminal stratum and registers with the one or more of the channels to form one or more conduits that extend through the sensor.

According to another aspect of the present invention there is provided a sensor for detecting the presence of a surface crack in a component, the sensor comprising:
  a base stratum that, in use, is affixed to the surface of the component, the base stratum having one or more channels that each extend through the thickness of the base stratum;
  at least one intermediate stratum that is affixed to two adjacent strata and has one or more holes and/or channels that each extend through the thickness of the intermediate stratum, each hole/channel registering with one or more of the holes/channels in an adjacent stratum;
  a terminal stratum that is affixed to the adjacent intermediate stratum, the terminal stratum having at least one hole that each extends through the thickness of the terminal stratum and registers with the one or more of the holes/channels in the adjacent intermediate stratum; and
  one or more conduits that extend through the sensor and are formed by the holes/channels in the base stratum, the at least one intermediate stratum and the terminal stratum.

According to yet another aspect of the present invention, there is provided a sensor for detecting the presence of a surface crack in a component, the sensor comprising:
  a base stratum that, in use, is affixed to the surface of the component, the base stratum having one or more channels that each extend through the thickness of the base stratum;
  at least one intermediate stratum that is affixed to two adjacent strata and has one or more holes and/or channels that each extend through the thickness of the intermediate stratum, each hole/channel registering with one or more of the holes/channels in an adjacent stratum;
  a terminal stratum that is affixed to the adjacent intermediate stratum;
  one or more first conduits that extend through the sensor and are formed by the holes/channels in the base stratum and the at least one intermediate stratum;
  an elongate lead that has a first stratum and a second stratum and one or more second conduits that extend in the elongate direction through the lead, each of the second conduits being in fluid communication with one of the first conduits.

BRIEF DESCRIPTION OF THE DRAWINGS

In order that the invention may be more easily understood, embodiments will now be described, by way of example only, with reference to the accompanying drawings, in which:
FIG. 7 is an exploded view of a sensor in accordance with a second embodiment of the present invention;
FIG. 8 is a side cross sectional view of the sensor in FIG. 7;
FIG. 9a is a schematic plan view of a base stratum of a sensor in accordance with a third embodiment of the present invention;
FIG. 9b is a schematic plan view of a first intermediate stratum of a sensor in accordance with the third embodiment;

FIG. 9c is a schematic plan view of a second intermediate stratum of the sensor in accordance with the third embodiment;

FIG. 9d is a schematic plan view of a terminal stratum of the sensor in accordance with the third embodiment;

FIG. 10 is a schematic plan view of the sensor of the third embodiment;

FIG. 10a is a cross sectional view of the sensor of FIG. 10, as viewed along the line B-B in FIG. 10;

FIG. 10b is a cross sectional view of the sensor of FIG. 10, as viewed along the line C-C in FIG. 10;

FIG. 23a is a schematic bottom view of a base stratum of a sensor in accordance with a ninth embodiment of the present invention;

FIG. 23b is a schematic top view of the base stratum of FIG. 23a;

FIG. 23c is a schematic bottom view of a terminal stratum of the sensor in accordance with the ninth embodiment;

FIG. 23d is a schematic top view of the terminal stratum of FIG. 23c;

FIG. 24 is a schematic plan view of the sensor of the ninth embodiment;

FIG. 24a is a cross sectional view of the sensor of FIG. 24, as viewed along the line B'-B' in FIG. 24; and FIG. 24b is a cross sectional view of the sensor of FIG. 24, as viewed along the line C'-C' in FIG. 24.

DETAILED DESCRIPTION OF THE PREFERRED EMBODIMENTS

Figure 1:
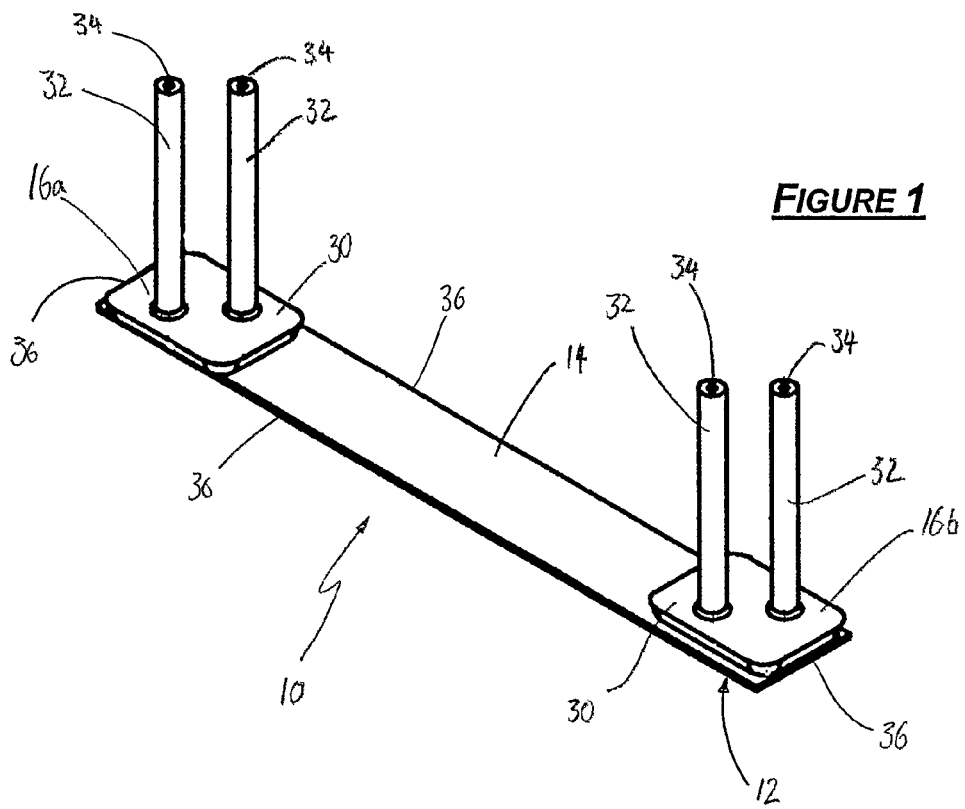
FIG. 1 is an axonometric view of a sensor in accordance with a first embodiment of the present invention.

FIGS. 1 to 6a show a sensor 10 in accordance with a first embodiment of the present invention. The sensor 10 has a base stratum 12, which has a first surface that in use can be affixed to a surface of a structure or component to be monitored, and an opposite second surface. The sensor 10 further has a terminal stratum 14, and two connectors 16a, 16b (hereinafter referred to collectively as "connectors 16"). The terminal stratum 14 has a first surface that is affixed to the base stratum 12, and an opposite second surface. Each of the connectors 16 is affixed to the second surface of the terminal stratum 14. Accordingly, the arrangement of the base stratum 12, terminal stratum 14 and the connectors 16 is such that the sensor 10 has a laminate, or laminate-like, structure.

The term "affixed" as appearing throughout this specification and claims, except where the context requires otherwise due to express language or necessary implication, is used to denote fixing to a specified surface or structure in a manner which forms or otherwise results in the creations of a substantially hermetic seal.

Figure 2:
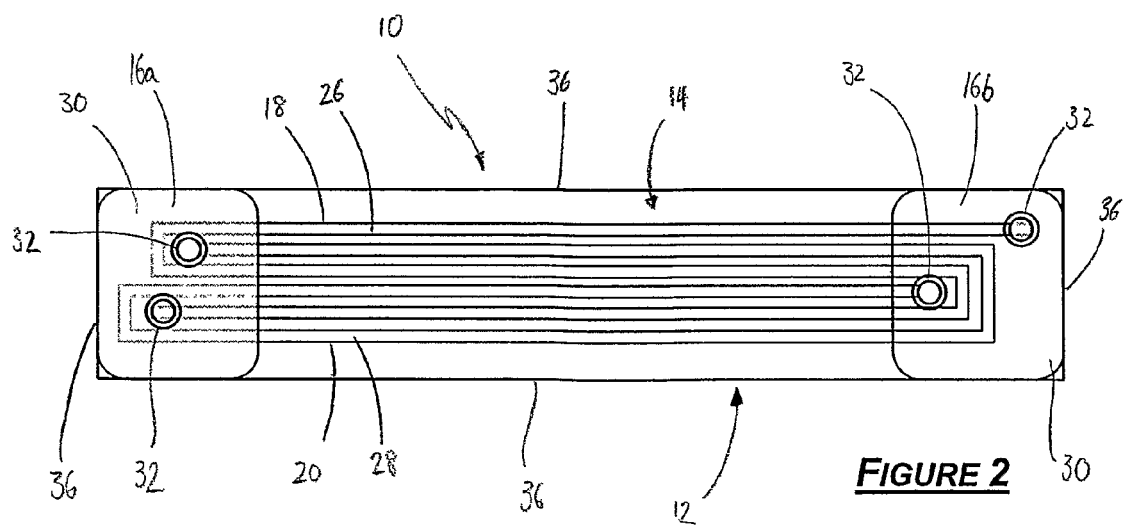
FIG. 2 is a schematic plan view of the sensor of FIG. 1.

FIG. 2 shows a plan view of the sensor 10 in which the connectors 16 and terminal stratum 14 are illustrated as being partially transparent to facilitate understanding of the alignment of the base stratum 12, the terminal stratum 14 and connectors 16 with respect to one another. It is to be appreciated that in practice, the base stratum 12, the terminal stratum 14 and/or connectors 16 may be made of either transparent or opaque materials.

Figure 3:
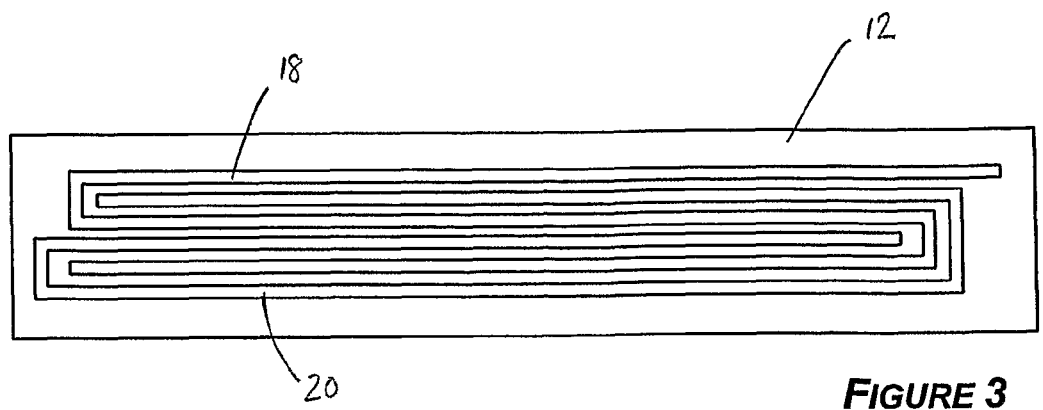
FIG. 3 is a schematic plan view of a base stratum of the sensor of FIG. 1.

FIG. 3 illustrates one form of the base stratum 12, which, in this embodiment, has a first and second channels 18, 20 that are cut, or otherwise formed, such that each of the first and second channels 18, 20 extends through the thickness of the base stratum 12. In this embodiment, each of the first and second channels 18, 20 are serpentine in their arrangement in the base stratum 12, such that the first channel 18 is intertwined with, but discrete from, the second channel 20. Therefore, when the sensor 10 is attached to the surface of a component that does not contain a flaw which intersects both the first and second channels 18, 20, the channels will be in fluid isolation from one another.

Figure 4:
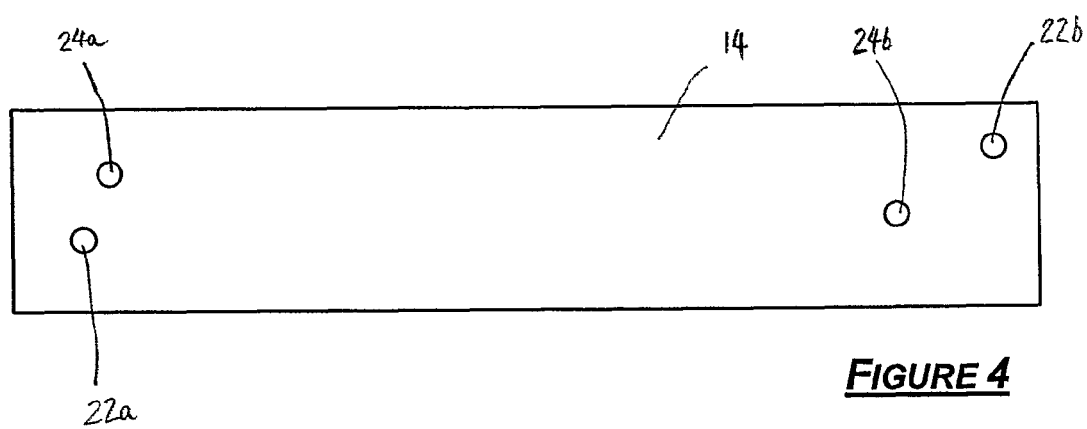
FIG. 4 is a schematic plan view of a terminal stratum of the sensor of FIG. 1.

FIG. 4 shows the terminal stratum 14 that, in this embodiment, has four holes 22a, 22b, 24a, 24b that extend through the thickness of the terminal stratum 14. A first pair of holes 22a, 22b are positioned within the terminal stratum 14 such that they both register with the first channel 18. Similarly, a second pair of holes 24a, 24b are positioned within the terminal stratum 14 such that they both register with the second channel 20. Further, in this embodiment, each hole 22a, 22b, 24a, 24b is positioned within the terminal stratum 14 such that each hole 22a, 22b, 24a, 24b registers with an end region of the respective first and second channel 18, 20.

The terminal stratum 14 extends across and is in contact with the base stratum 12. Each of the first and second channels 18, 20 and the respective holes 22a, 22b, 24a, 24b form two conduits 26, 28 (as shown in FIG. 2) within the sensor 10. A first conduit 26 is formed by the first channel 18 and first pair of holes 22a, 22b. Similarly, a second conduit 28 is formed by the second channel 20 and second pair of holes 24a, 24b. As shown in FIG. 2, each of the conduits 26, 28 are provided within the sensor 10. When the sensor 10 is affixed to a surface, each conduit 26, 28 is substantially hermetically sealed due to the base stratum 12 being affixed to the surface and the terminal stratum 14 being affixed to the base stratum 12.

Figure 5A:
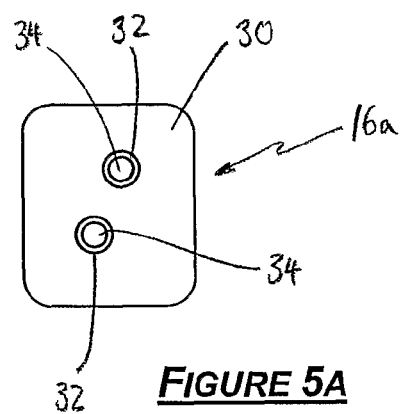
FIG. 5a is a schematic plan view of a first connector of the sensor of FIG. 1.
Figure 5B:
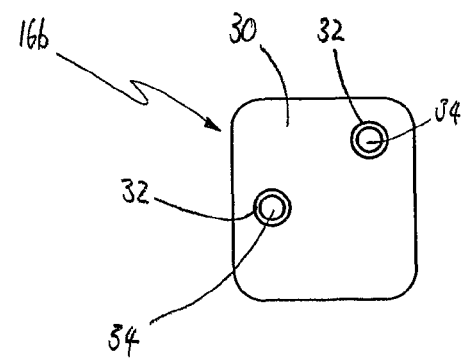
FIG. 5b is a schematic plan view of a second connector of the sensor of FIG. 1.

As shown in FIGS. 1, 5a and 5b, each of the connectors 16 has a flanged portion 30 that is affixed to the terminal stratum 14. Connection tubes 32 extend from the flanged portion 30 away from the terminal stratum 14. Each tube 32 defines a passage or throughway 34 that extends through both the length of the respective tube 32 and the flanged portion 30. Each throughway 34 registers with a respective one of the holes 22a, 22b, 24a, 24b in the terminal stratum 14. Tubing, such as flexible piping or the like (not shown) can be connected to each of the tubes 32 to plumb the sensor 10 to elements within a differential pressure monitoring system, such as the instrumentation (also not shown) of a vacuum monitoring system, or other like sensors 10.

Figure 6:
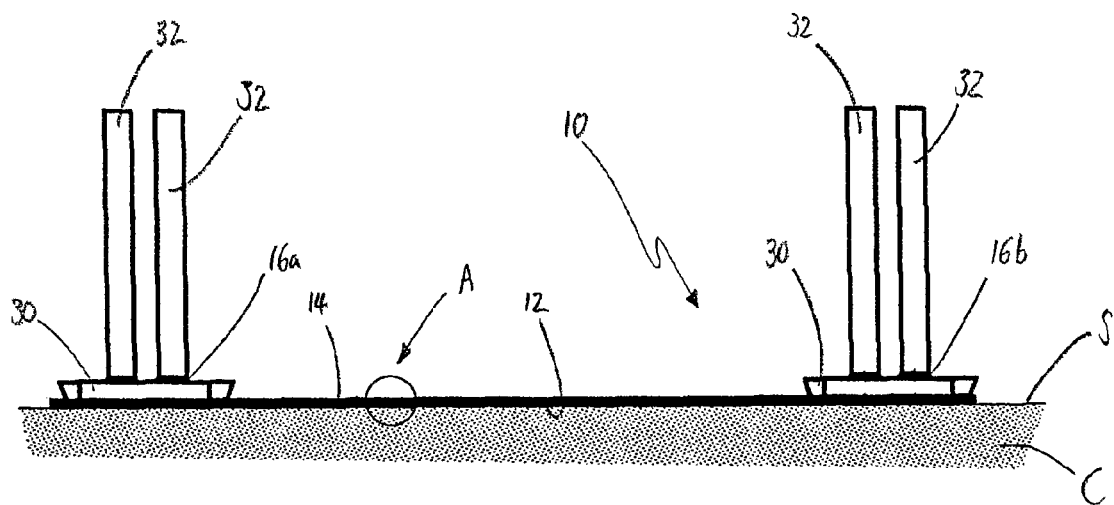
FIG. 6 is a side view of the sensor of FIG. 1 affixed to a component.
Figure 6A:
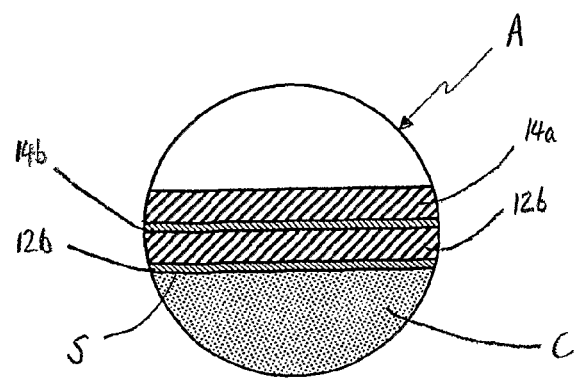
FIG. 6a is an enlarged view of detail A of FIG. 6.

FIG. 6 shows the sensor 10 affixed to a surface S of a component C to be monitored. As shown in FIG. 6a, each of the base stratum 12 and terminal stratum 14 is in the form of a film 12a, 14a and an adhesive 12b, 14b on one side of the respective film. The film 12a, 14a may be, for example, plastics material. One suitable plastics material is a fluoropolymer. The adhesive can conveniently be a pressure sensitive adhesive. Prior to application of the sensor 10 to the surface of a component, the adhesive 12b of the base stratum 12 can be covered with a release paper (not shown) to provide protection to the adhesive 12b.

Similarly, the surface of the flange 30 that is remote from the tubes 32 is affixed to the surface of the terminal stratum 14 that is remote from the base stratum 12. For example, an adhesive may be used to affix the connector 16 to the terminal stratum 14.

The thickness of each of the base and terminal stratum 12, 14 may be less than 5 mm. In some embodiments, the thickness of each of the base and terminal strata 12, 14, inclusive of both the film 12a, 14a and adhesive 12b, 14b, can be 175 µm or less. It is to be appreciated that the thickness of each of the base and terminal strata 12, 14 is one of the factors that determine the volume of the first and second channels 18, 20. Furthermore, where the sensor 10 is used in a differential pressure monitoring system the volume of each of the first and second channels 18, 20 influences the acquisition time of measurement indicating the presence of a crack at the surface of the component on which the sensor 10 is installed. In the embodiment shown in FIG. 1 to 6a, the thickness of the adhesive 12b, 14b is approximately 50 µm or less. In FIGS. 1 to 6 the adhesive has been omitted for clarity.

In use, the sensor 10 is applied to the surface S of a component C. The adhesive 12b of the base stratum 12 affixes the sensor 10 to the surface and forms a seal between the base stratum 12 and the surface S such that each of the first and second channels 18, 20, and thus the conduits 26, 28, can be substantially in fluid isolation with respect to atmospheric air. The sensor 10 may be plumbed via the tubes 32 of the connectors 16 to, for example, the instrumentation of a vacuum monitoring system.

A relative vacuum pressure state can be created in one or both of the first and second channels 18, 20. A crack in the component that opens onto the surface and intersects one or both of the first and second channels 18, 20 will allow fluid flow between the crack and the respective first and/or second channels 18, 20. Where a pressure differential exists between two regions of the crack, such a fluid flow will occur. Accordingly, a change in fluid flow (and/or a change in pressure state of the respective first and/or second channels 18, 20) can be indicative of the presence of a crack.

A crack may extend from a region beyond one of the peripheral edges 36 of the sensor 10 and intersect one or both of the first and second channels 18, 20. In an embodiment in which there is a pressure differential between the atmosphere surrounding the sensor 10 and the conduits 26, 28, fluid flow through the crack may occur.

Alternatively or additionally, a crack may intersect the first and second channels 18, 20. In an embodiment in which there is a pressure differential between the conduits 26, 28, fluid flow through the crack may occur.

Clearly, the separation of the channels 18, 20 of the sensor 10, and similarly the distance between the peripheral edges 36 and the channels 18, 20, are factors that influence the minimum crack length that can be detected by the sensor 10.

FIGS. 7 and 8 illustrate a sensor 110 in accordance with a second embodiment. The sensor 110 has a base stratum 112 and a terminal stratum 114. The sensor 110 further has a connector 116. The arrangement of the base stratum 112, terminal stratum 114 and the connector 116 is such that the sensor 110 is in the form of a laminate, or laminate-like, structure. The connector 116 fulfills the function of the connectors 16a, 16b in the sensor 10.

The base stratum 112 is provided with two channels 118, 120, which extend through the thickness of the base stratum 112 and which, in this embodiment, are parallel and linear.

The terminal stratum 114 is provided with four holes 122a, 122b, 124a, 124b, each of which extends through the thickness of the terminal stratum 114. Furthermore, each of the four holes 122a, 122b, 124a, 124b in the terminal stratum 114 registers with a respective one of the two channels 118, 120, at an end region thereof.

The connector 116 has a flange 130 that is affixed to the terminal stratum 114. As shown in FIGS. 7 and 8, the flange 130 extends across the terminal stratum 114. Four tubes 132 extend from the flange 130, each of which registers with one of the holes 122a, 122b, 124a, 124b in the terminal stratum 114. Each tube 132 defines a throughway that extends through both the respective tube 132 and the flange 130. It will be appreciated that, in this embodiment, the terminal stratum 114 may be omitted as the function of covering and sealing each of the channels 118, 120 in the base stratum 112 can alternatively be fulfilled by the flange 130.

A first conduit 126 is formed within the sensor 110 by the first channel 118 and first pair of holes 122a, 122b. Similarly, a second conduit 128 is formed by the second channel 120 and second pair of holes 124a, 124b. When the sensor 110 is affixed to a surface, each conduit 126, 128 is substantially hermetically sealed due to the base stratum 112 being affixed to the surface and the terminal stratum 114 being affixed to the base stratum 112.

As shown in FIG. 8, each of the base stratum 112, the terminal stratum 14 and the connector stratum 116 is in the form of a film 112a, 114a, 116a of, for example, plastics material together with an adhesive 112b, 114b, 116b on one side of the respective film. The plastics material of the film may be, for example, a fluoropolymer. The adhesive can conveniently be a pressure sensitive adhesive. Prior to application of the sensor 110 to the surface S of a component C, the adhesive 112a on the base stratum 112 can be covered with a release paper (not shown) to provide protection.

As the two channels 118, 120 are parallel and linear, the sensor 110 is ideally suited to being connected to a component C at a location where a crack commonly occurs, and the likely crack growth direction is known. The sensor 110 can be installed to simply detect the presence of a surface crack in the component C that intercepts one of the two channels 118, 120. This may be achieved by maintaining the conduits 126, 128 at a common pressure level that is either above or below the atmospheric pressure surrounding the sensor 110. A crack that extends from the a region outside the peripheral edges 136 of the sensor 110 and intercepts one or both of the channels 118, 120 can be detected by the change in pressure state of one or both of the conduits 126, 128 or by the change in fluid flow to or from the one or both of the conduits 126, 128.

Alternatively, the sensor 110 can be installed on a component C and within a differential pressure measurement system, which includes the sensor 110, and arranged such that a differential pressure is maintained between the conduits 126, 128. The presence of a crack that intercepts both channels 118, 120 may cause a fluid flow between the conduits 126, 128 and/or a change in the pressure state in each of the conduits 126, 128.

In a further alternative, the sensor 110 can be installed on a component C and within a differential pressure measurement system, which includes the sensor 110, and arranged to determine not only the presence of a crack, but also the rate of crack growth. For example, a differential pressure can be established between the conduits 126, 128 and the atmosphere such that the pressure in each of the conduits 126, 128 is either above or below the atmospheric pressure surrounding the sensor 110. A crack that extends through the component C from a region on the surface S of the component C and outside the peripheral edges 136, and intersects one of the channels 118, 120 will cause a first fluid flow to occur between the respective conduit 126, 128 and the atmosphere. Should the crack grow and intersect the other of the channels 120, 118, a second fluid flow will occur through the crack between the two first and second conduits 126, 128, and the atmosphere. The change in fluid flow and/or pressure states in the conduits 126, 128 may indicate the presence of a crack.

It is to be appreciated that an apparent rate of crack growth and/or an apparent crack length that is determined if the crack growth direction is oblique to one or both of the first and second channels 118, 120. Therefore, the sensor 110 is ideally installed such that the first and second channels 118, 120 are perpendicular to the likely crack growth direction. Accordingly, the actual rate of crack growth and/or actual crack length at the surface S of the component C can be determined.

FIGS. 9a to 9d respectively show schematically a base stratum 212, a first intermediate stratum 213a, a second intermediate stratum 213b and a terminal stratum 214 of a sensor 210 in accordance with a third embodiment. As shown in FIG. 9a, the base stratum 212 has a plurality of first channels 218, each of which extends through the thickness of the base stratum 212. The base stratum 212 further has a plurality of second channels 220, each of which extends through the thickness of the base stratum 212. In this embodiment, each of the first and second channels 218, 220 are elongate and linear. Furthermore, the first and second channels 218, 220 are all parallel and each are of equal separation with respect to their adjacent first and second channels 218, 220. In this embodiment, each of the first channels 218 is longer than the second channels 220 such that the ends of the first channels 218 extend beyond the ends of the second channels 220.

The first intermediate stratum 213a (which is shown in FIG. 9b) is affixed to the base stratum 212. The first intermediate stratum 213a has a plurality of first apertures in the form of holes 238 that extend through the thickness of the first intermediate stratum 213a. Each of the first holes 238 registers with an end of one of the second channels 220.

In addition, the first intermediate stratum 213a has a plurality of second apertures in the form of holes 240a and a plurality of channels 240b that each extend through the thickness of the first intermediate stratum 213a. The second holes 240a each register with one end of one of the first channels 218. The channels 240b are elongate, and each register with the ends of two of the first channels 218 such that the respective two first channels 218 are in fluid communication via one of the channels 240b.

The second intermediate stratum 213b (which is shown in FIG. 9c) is affixed to the first intermediate stratum 213a. The second intermediate stratum 213a has a plurality of first holes 242 that extend through the thickness of the second intermediate stratum 213b. Each of the first holes 242 registers with one of the second holes 240a in the first intermediate stratum 213a.

In addition, the second intermediate stratum 213b has a plurality of second holes 244a and a plurality of channels 244b that each extend through the thickness of the second intermediate stratum 213b. The second holes 244a each register with one end of one of the first holes 238 in the first intermediate stratum 213a. The channels 244b are elongate, and each registers with two of the first holes 238 in the first intermediate stratum such that the respective two first holes 238 are in fluid communication via one of the channels 244b.

The terminal stratum 214 (which is shown in FIG. 9d) is affixed to the second intermediate stratum 213b. The terminal stratum 214 has first holes 246 that each register with one of the first holes 242 in the second intermediate stratum 213b. The terminal stratum 214 further has second holes 248 that each register with one of the second holes 244a in the second intermediate stratum 213b.

For clarity connectors to connect the sensor 210 within a differential pressure monitoring system have been omitted. However, it is to be appreciated that, in some embodiments, connectors similar to the connectors 16, 116 may be affixed to the terminal stratum 214 to plumb the sensor 210 to other elements within a monitoring system, such as other sensors and/or instrumentation.

FIG. 10 shows schematically the sensor 210 in plan view, in which each of the first intermediate stratum 213a, the second intermediate stratum 213b and the terminal stratum 214 have been illustrated in transparent form for clarity. FIG. 10a shows a cross sectional view of the sensor 210 as viewed along the line B-B in FIG. 10. FIG. 10b shows a cross sectional view of the sensor 210 as viewed along the line C-C in FIG. 10.

A first conduit 226 is formed by the first channels 218, the second holes 240a and channels 240b in the first intermediate stratum 213a, the first holes 242 in the second intermediate stratum 213b, and the first holes 246 in the terminal stratum 214. Similarly, a second conduit 228 is formed by the second channels 220, the first holes 238 in the first intermediate stratum 213a, the second holes 244a and channels 244b in the second intermediate stratum 213b, and the second holes 248 in the terminal stratum 214.

As can be seen in FIGS. 10, 10a and 10b, the laminate structure of the sensor 210 is such that two conduits are formed within the sensor 210. When the base stratum 212 of the sensor 210 is affixed to the surface S of a component C that is intact (that is, no surface cracks that intersect the sensor 210 are present), each conduit 226, 228 is in fluid isolation from the atmosphere and also one another. Each conduit 226, 228 is of serpentine path arrangement, in directions both parallel and perpendicular to the surface S, within the sensor 210 and respectively between the first holes 246 and the second holes 248 in the terminal stratum 214.

The sensor 210 can be plumbed into a differential pressure monitoring system, which can be operated such that a differential pressure exists between the conduits 226, 228. For example, the conduits 226, 228 may be evacuated to establish a relative vacuum (with respect to the atmosphere), while the second or first channels 220, 218 are maintained at atmospheric pressure. The presence of a surface crack in the component C that intersects at least one of the first channels 218 and at least one of the second channels 220 will result in a fluid flow between the respective first and second channels 218, 220. Accordingly, the presence of the crack will be apparent by the fluid flow, and/or change in pressure of the first and/or first and second channels 218, 220.

As the first conduit 226 is continuous between the first holes 246, it is possible to test for a blockage in the conduit 226. A blockage indicates that continuity does not exist through the conduit 226, and that portions of the sensor 210 are inactive. Clearly, a crack that intercepts an inactive portion of the conduit 226 will not be detected. Similarly, the second conduit 228 is continuous between the second holes 248; thus, continuity of second conduit 228 may also be tested. For example, a continuity test may be achieved by introducing fluid into one of the conduits 226, 228 via one of the holes 246, 248 and monitoring the steady state flow of fluid exhausted via the corresponding other holes 246, 248.

Figure 11:
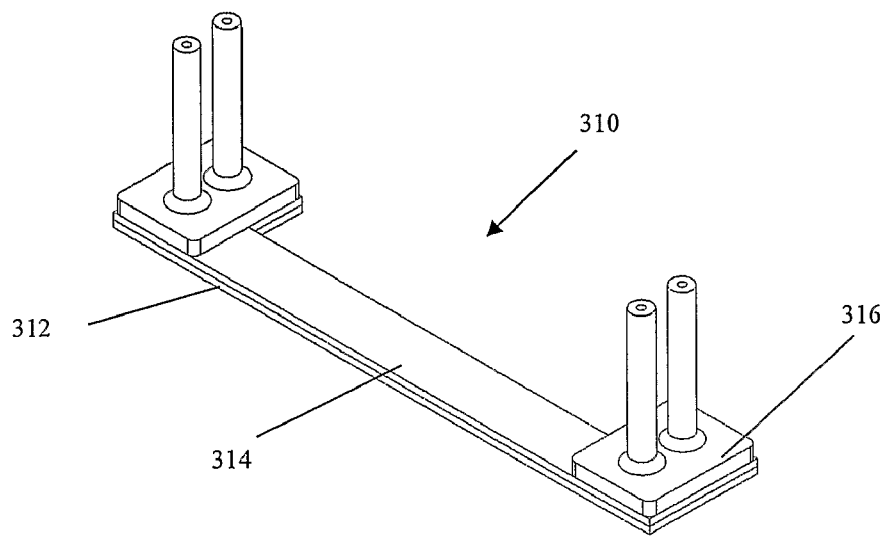
FIG. 11 is an axonometric view of a sensor in accordance with a fourth embodiment of the present invention.
Figure 12:
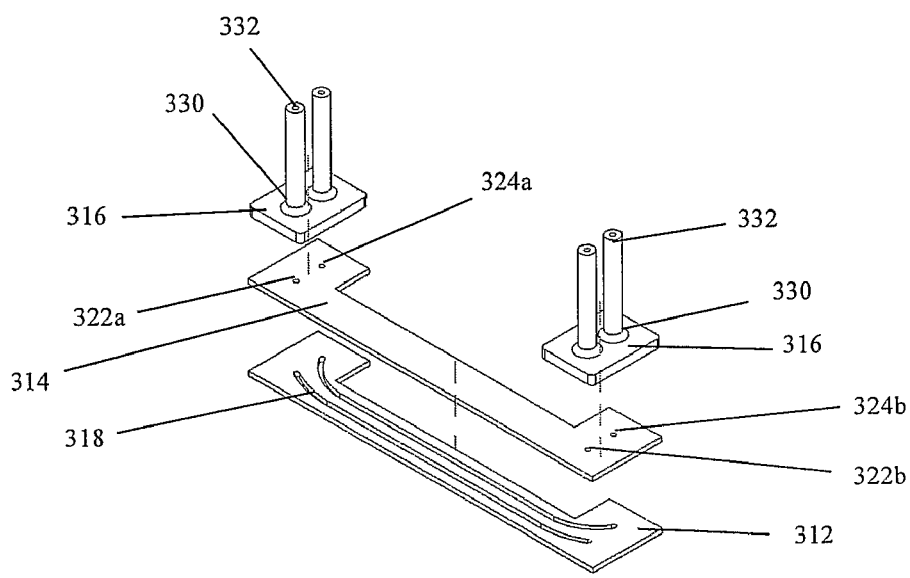
FIG. 12 is an exploded view of the sensor of FIG. 11.
Figure 13:
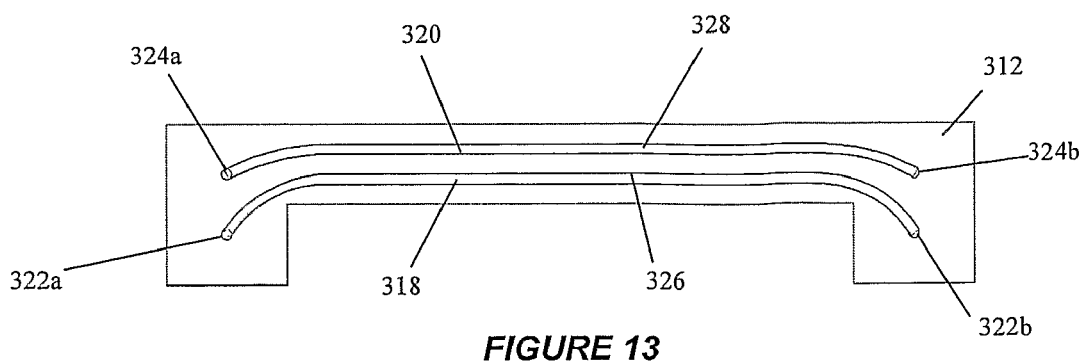
FIG. 13 is a bottom view of the sensor of FIG. 11.
Figure 14:
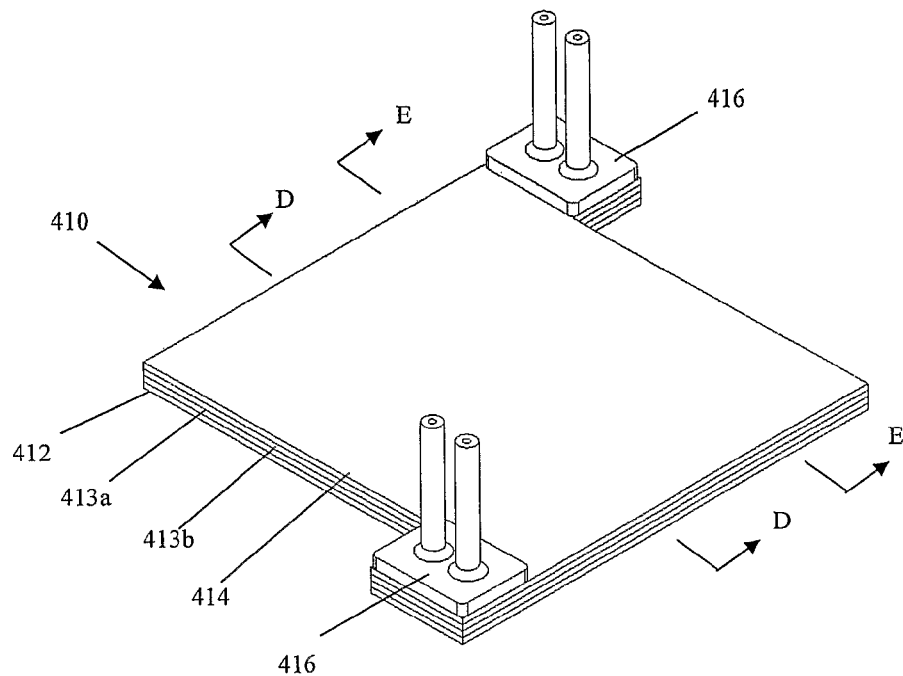
FIG. 14 is an axonometric top view of a sensor in accordance with a fifth embodiment of the present invention.

FIGS. 11 to 13 show a sensor 310 in accordance with a fourth embodiment. The sensor 310 has a base stratum 312, which has a first surface that in use can be affixed to a surface of a structure S of a component C to be monitored, and an opposite second surface. The sensor 310 further has a terminal stratum 314, and two connectors 316. The terminal stratum 314 has a first surface that is affixed to the base stratum 312, and an opposite second surface. Each of the two connectors 316 is affixed to the second surface of the terminal stratum 314. The arrangement of the base stratum 312, terminal stratum 314 and the connectors 316 is such that the sensor 310 is in the form of a laminate, or laminate-like, structure.

The base stratum 312 is provided with two channels 318, 320, which extend through the thickness of the base stratum 312. In this embodiment, portions of the two channels 318, 320 are arcuate and non-parallel.

The terminal stratum 314 is provided with four holes 322a, 322b, 324a, 324b, each of which extends through the thickness of the terminal stratum. Furthermore, each of the four holes 322a, 322b, 324a, 324b in the terminal stratum 314 registers with a respective one of the two channels 318, 320, at an end region thereof.

A first conduit 326 is formed within the sensor 310 by the first channel 318 and first pair of holes 322a, 322b. Similarly, a second conduit 328 is formed by the second channel 320 and second pair of holes 324a, 324b.

The two connectors 316 each have a flange 330 that is affixed to the terminal stratum 314. Two tubes 332 extend from the flange 330 of each connector 316, such that one tube 332 registers with one of the holes 322a, 322b, 324a, 324b in the terminal stratum 314.

It is to be appreciated that the channels of a sensor may be arcuate such that the channels in the base stratum, when the sensor is affixed to a component, encircle a feature in the component. Furthermore, the peripheral shape of the sensor itself may be any desired shape to suit the intended application. For example, a component having a fillet of relatively small radius that experiences high stress concentration, which may commonly produce a crack emanating from the fillet. In such a component, it may be desirable to monitor for the presence of a crack in the component by applying a single sensor according to an embodiment of the present invention, the sensor having arcuate channels in the base stratum. In addition, it may be desirable for the embodiment of the sensor to be of a generally "kidney" shape.

Figure 15:
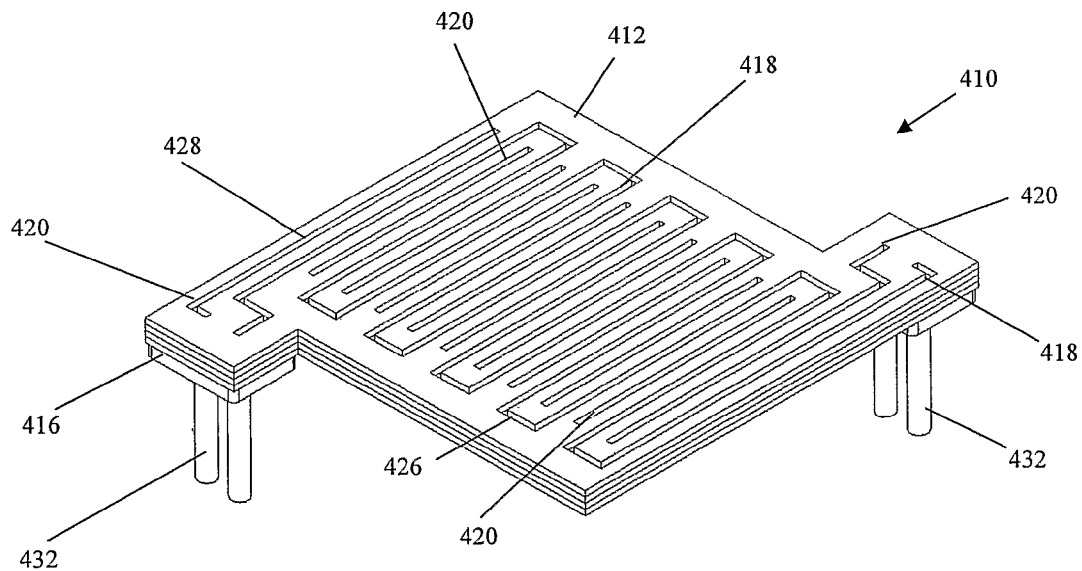
FIG. 15 is an axonometric bottom view of the sensor of FIG. 14.
Figure 16:
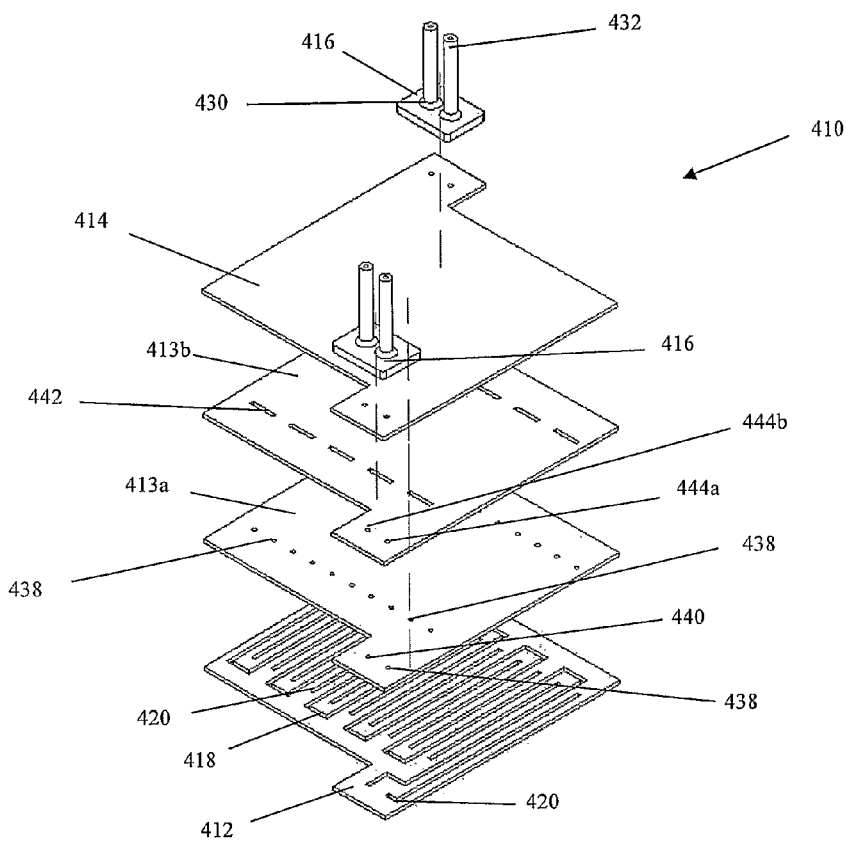
FIG. 16 is an exploded view of the sensor of FIG. 14.
Figure 17:
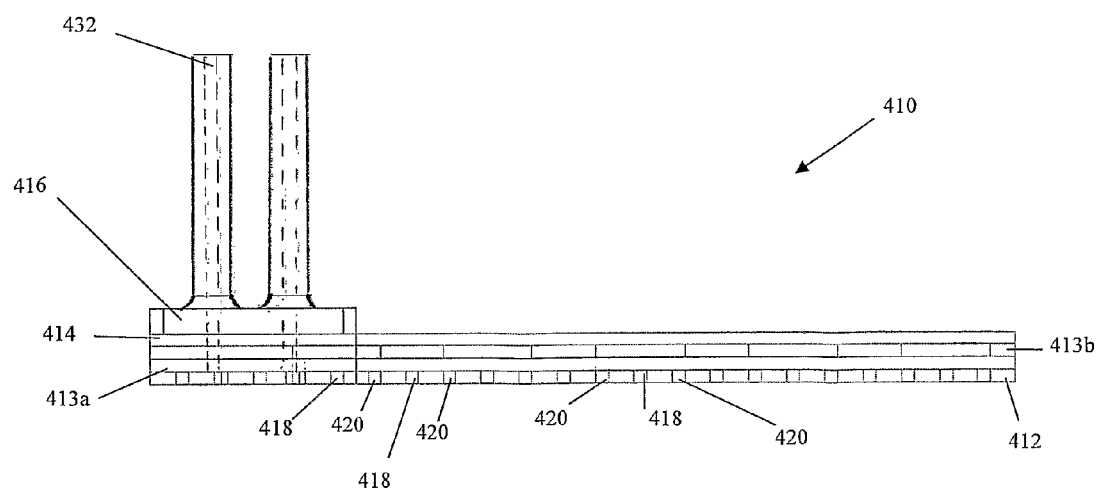
FIG. 17 is a side cross sectional view of the sensor of FIG. 14, as viewed along section D-D in FIG. 14.
Figure 18:
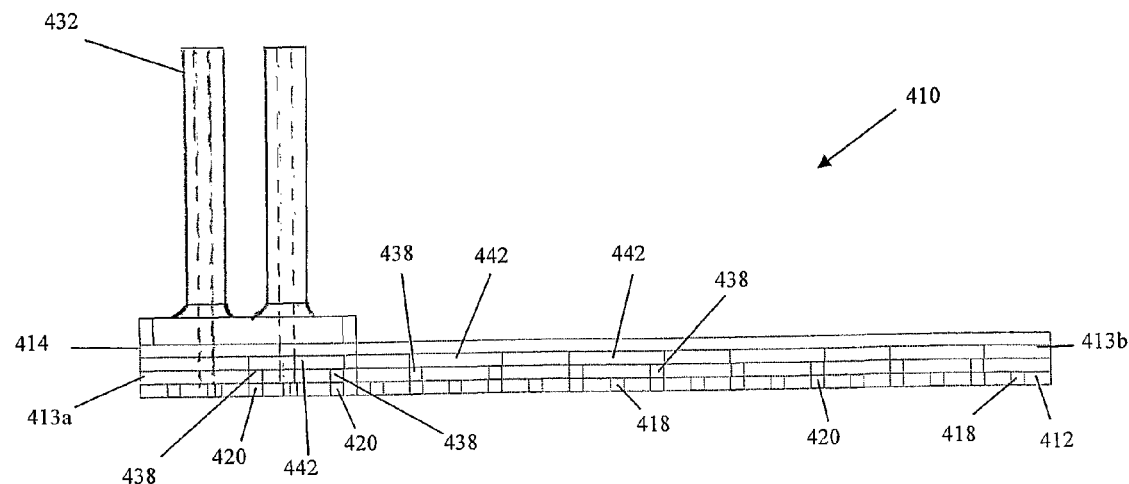
FIG. 18 is a side cross sectional view of the sensor of FIG. 14, as viewed along section E-E in FIG. 14.

FIGS. 14 to 19 show a sensor 410 according to a fifth embodiment. The sensor 410 has a base stratum 412, a first intermediate stratum 413a, a second intermediate stratum 413b and a terminal stratum 414. The base stratum 412 has a first channel 418 that extends through the thickness of the base stratum 412. As shown in FIG. 15, the first channel 418 is elongate and serpentine in its arrangement in the plane of the base stratum 412.

The base stratum 412 further has a plurality of second channels 420, each of which extends through the thickness of the base stratum 412. In this embodiment, each of the second channels 420 is interposed between portions of the first channel 418.

The first intermediate stratum 413a is affixed to the base stratum 412. The first intermediate stratum 413a has a plurality of second holes 438 that extend through the thickness of the first intermediate stratum 413a. Each of the second holes 438 registers with an end of one of the second channels 420.

In addition, the first intermediate stratum 413a has two first holes 440 that each extend through the thickness of the first intermediate stratum 413a. The first holes 440 each register with one end of the first channel 418.

The second intermediate stratum 413b is affixed to the first intermediate stratum 413a. The second intermediate stratum 413a has a plurality of channels 442 that extend through the thickness of the second intermediate stratum 413b. Each of the channels 442 registers with one of the second holes 438 in the first intermediate stratum 413a. Furthermore, each of the channels 442 connects two of the second holes 438 in the first intermediate stratum 413a such that the respective two second holes 438 are in fluid communication.

In addition, the second intermediate stratum 413b has two second holes 444a that each extend through the thickness of the second intermediate stratum 413b. The second holes 444a each register with one end of one of the second holes 438 in the first intermediate stratum 413a. The second intermediate stratum 413b further has two first holes 444b that each register with one of the first holes 440 in the first intermediate stratum 413a.

The terminal stratum 414 is affixed to the second intermediate stratum 413b. The terminal stratum 414 has second holes 446 that each register with one of the second holes 444a in the second intermediate stratum 413b. The terminal stratum 414 further has first holes 448 that each register with one of the first holes 444b in the second intermediate stratum 413b.

The sensor 410 has two connectors 416 that are each affixed to the terminal stratum 414. Each of the connectors 416 is in the form of a flanged portion 430 that is affixed to the terminal stratum 414. Connection tubes 432 extend from the flanged portion 430 away from the terminal stratum 414. Each tube 432 registers with a respective one of the holes 446, 448 in the terminal stratum 414.

Tubing, such as flexible piping or the like (not shown) can be connected to each of the tubes 432 to plumb the sensor 410 to elements within a differential pressure monitoring system.

In summary, in the embodiment of the sensor 410 shown in FIGS. 14 to 19, the first channel 418 is in fluid communication with one of the tubes 432 in each connector 416 as follows:

two of the tubes 432 (one in each connector 416) each register with the first holes 448 in the terminal stratum 414;

the first holes 448 in the terminal stratum 414 each register with one of the first holes 444b in the second intermediate stratum 413b;

the first holes 444b in the second intermediate stratum 413b each register with one of the first holes 440 in the first intermediate stratum 413a; and the first holes 440 in the first intermediate stratum 413a each register with an end of the first channel 418 in the base stratum 412.

Similarly, the second channels 420 are in fluid communication with one of the tubes 432 in each connector 416 as follows:

two of the tubes 432 (one in each connector 416) each register with the second holes 446 in the terminal stratum 414;

the second holes 446 in the terminal stratum 414 each register with either one of the channels 442 or one of the second holes 444a in the second intermediate stratum 413b;

the channels 442 in the second intermediate stratum 413b each register with two of the second holes 438 in the first intermediate stratum 413a, and the second holes 444a each register with one of the second holes 438 in the first intermediate stratum 413a; and the second holes 438 in the first intermediate stratum 413a each register with an end of one of the second channels 420 in the base stratum 412.

A first conduit 426 is formed by the first channel 418, the first holes 440 in the first intermediate stratum 413a, the first holes 444b in the second intermediate stratum 413b, and the first holes 448 in the terminal stratum 414. Similarly, a second conduit 428 is formed by the second channels 420, the second holes 438 in the first intermediate stratum 413a, the second holes 444a and channels 442 in the second intermediate stratum 413b, and the second holes 446 in the terminal stratum 414.

As the first channel 418 is serpentine in its arrangement in the base stratum 412, the first conduit 426 is also generally serpentine in its arrangement within the sensor 410. The second conduit 428 is of generally serpentine arrangement within the sensor 410, in directions both parallel and perpendicular to the surface of the base stratum 412.

Figure 19:
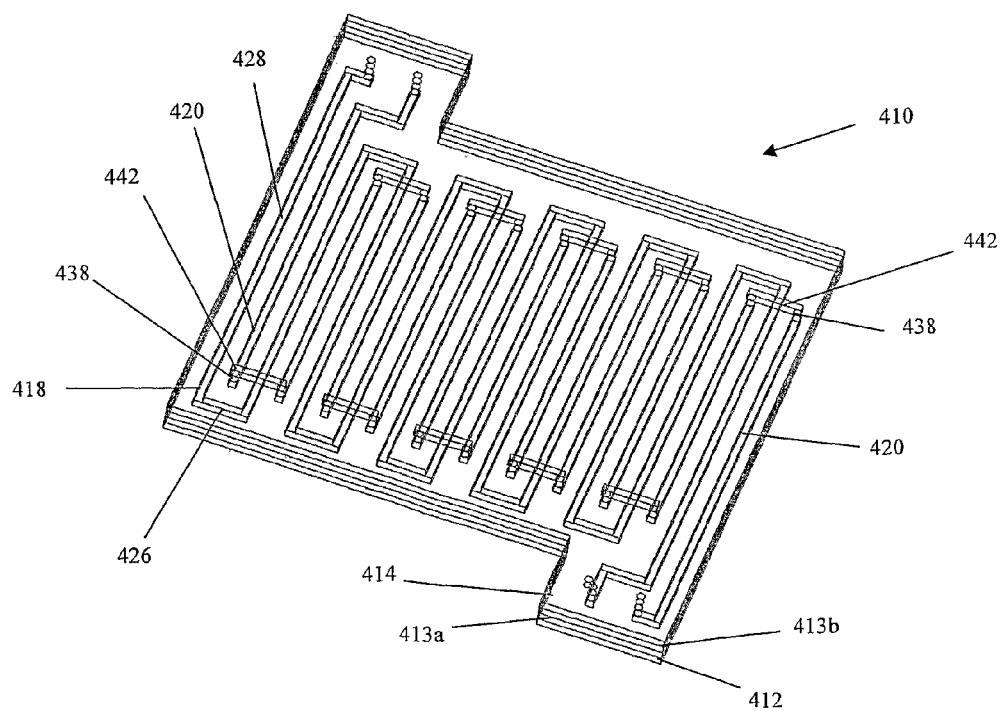
FIG. 19 is a schematic view of the sensor of FIG. 14.

FIG. 19 shows an axonometric view of the sensor 410 (with the connectors 416 omitted for clarity) in which the base stratum 412, first intermediate stratum 413a, second intermediate stratum 413b and terminal stratum 414 are transparent to facilitate understanding of the relative alignment the respective strata 412, 413a, 413b, 414 with respect to one another. It is to be appreciated that in practice, the respective strata 412, 413a, 413b, 414 may be made of either transparent or opaque materials, or a combination thereof.

Figure 20:
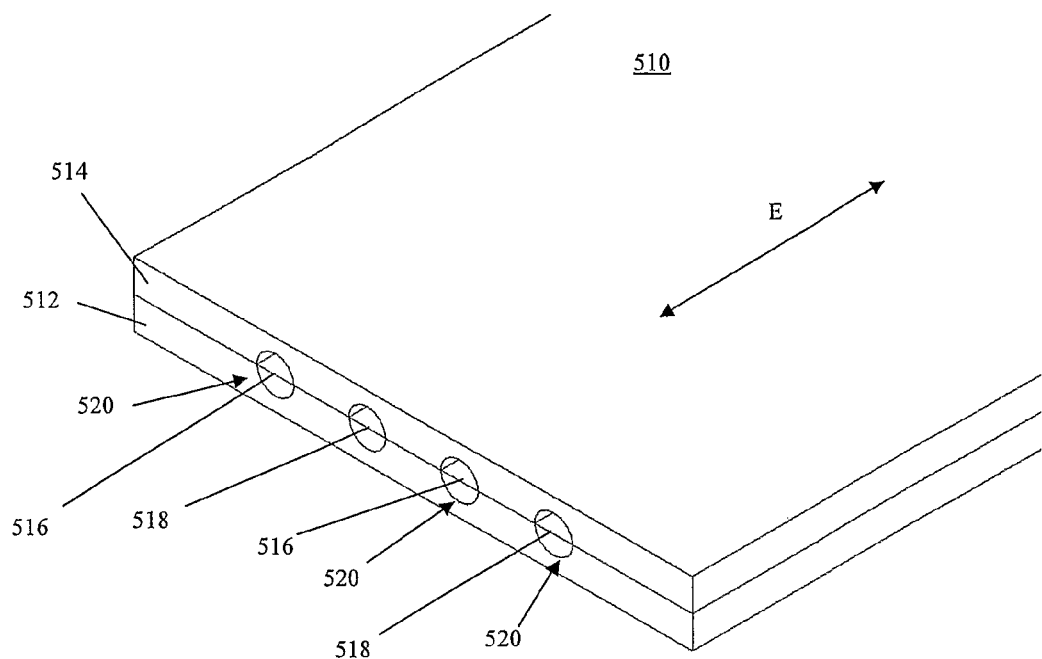
FIG. 20 is a cross sectional axonometric view of a lead in accordance with a sixth embodiment of the present invention.

FIG. 20 shows a cross sectional axonometric view of a lead 510 in accordance with a sixth embodiment. The lead 510 is elongate in the direction indicated by double-headed arrow E. Accordingly, the lead 510 as viewed in FIG. 20 has been sectioned in a direction transverse to the elongate direction of the lead 510.

The lead 510 may be used to plumb a sensor, such as the sensors of the first to fifth embodiments, within a differential pressure monitoring system, to the instrumentation of the system. Alternatively or additionally, the lead 510 may be used to plumb a sensor to other sensors within the system.

As shown in FIG. 20, the lead 510 has a first stratum 512 that is elongate and generally flat, such that the first stratum 512 has a generally ribbon-like shape. The lead 510 further has a second stratum 514 that is also of generally ribbon-like shape. The first stratum 512 is affixed to the second stratum 514 such that the lead 510, in this embodiment, also has a generally ribbon-like shape.

The first stratum 512 has a plurality of grooves 516, which are provided in the surface that is adjacent to the second stratum 514. The grooves 516 extend partially through the thickness of the first stratum 512. In this embodiment each of the grooves 516 is semi-circular in cross section when viewed in the elongate direction E. Similarly, the second stratum 514 has a plurality of grooves 518, which are provided in the surface that is adjacent the first stratum 512. The second grooves 518 extend partially through the thickness of the second stratum 514. The relative position of grooves 516, 518 in their respective stratum 512, 514 is such that the grooves 516, 518 register with one another. In this embodiment, each of the grooves 518 is also semi-circular in cross section when viewed in the elongate direction E. Accordingly, each of the grooves 516 registers with one of the grooves 518 to form a conduit 520 that extends in the elongate direction E within the lead 510. Therefore, in this embodiment each conduit 520 has a generally circular cross section when viewed in the elongate direction E. As shown in FIG. 20, the lead 510 in this embodiment has four conduits 520.

The lead 510 can be connected to a sensor of laminate construction by laminating the first and second strata 512, 514 within the laminate structure of the sensor. For example, an end portion of the lead 510, which has conduits 520 opening onto and end face of the lead 510, can be affixed to one or more strata of the sensor. Conduits within the sensor can be arranged to bring the various channels in the base stratum of the sensor in fluid communication with the conduits 520 of the lead 510 via the openings on the end face of the lead 510. In such an embodiment a terminal stratum may be in the form of a continuous sheet.

Alternatively, the lead 510 can be connected to a sensor of laminate construction that has holes in the terminal stratum. One of the first or second strata 512, 514 of the lead is provided with holes/elongate channels (not shown) that extend through the thickness of the respective first or second strata 512, 514 in a direction that is transverse to the conduits 520. Each of the holes/elongate channels registers with one of the holes in the terminal stratum of the sensor. A portion of the respective first or second stratum 512, 514 about the holes/elongate channels is affixed to the terminal stratum of the sensor. In an embodiment of the lead 510 in which the conduits 520 open on to an end face of the lead 510, portions of the conduits 520 adjacent the end face may need to be closed off or otherwise sealed.

In a further alternative, the lead 510 can be connected to a sensor having a connector, such as the connector 16 illustrated in FIG. 1. Each of the tubes 32 of the connector 16 can be inserted into an end portion one of the conduits 520 through an opening in the end face of the lead 510. Each tube 32 may be affixed to the lead 510 using an sealant/adhesive.

Figure 21:
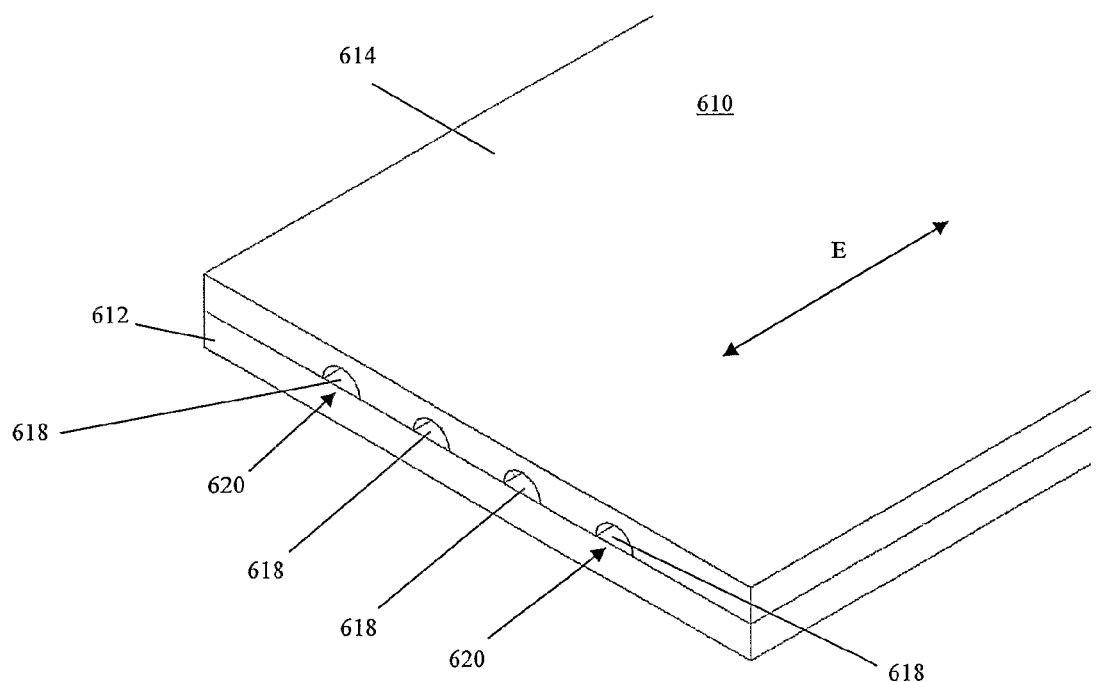
FIG. 21 is a cross sectional axonometric view of a lead in accordance with a seventh embodiment of the present invention.

FIG. 21 shows a cross sectional axonometric view of a lead 610 in accordance with a seventh embodiment. The lead 610 is elongate in the direction indicated by double-headed arrow E. Accordingly, the lead 610 as viewed in FIG. 21 has been sectioned in a direction transverse to the elongate direction E of the lead 510.

As shown in FIG. 21, the lead 610 has a first stratum 612 that is elongate and generally flat, such that the first stratum 612 has a generally ribbon-like shape. The lead 610 further has a second stratum 614 that is also of generally ribbon-like shape. The first stratum 612 is affixed to the second stratum 614 such that the lead 610, in this embodiment, also has a generally ribbon-like shape.

In this embodiment, the second stratum 614 alone is provided with a plurality of grooves 618, which are provided in the surface that is adjacent the first stratum 612. The grooves 618 extend partially through the thickness of the second stratum 614. That is, in contrast to the embodiment shown in FIG. 20, the first stratum 612 is not provided with grooves. Accordingly, in the embodiment illustrated in FIG. 21, each of the grooves 618 is also semi-circular in cross section when viewed in the elongate direction E. Conduits 620 that extend in the elongate direction within the lead 610 are formed by the grooves 618. Therefore, in this embodiment, each conduit 620 has a cross section of a generally circular sector shape when viewed in the elongate direction E.

The lead 610 may be connected to a sensor in any desired manner, for example, such as described in connection with the lead 510.

Figure 22:
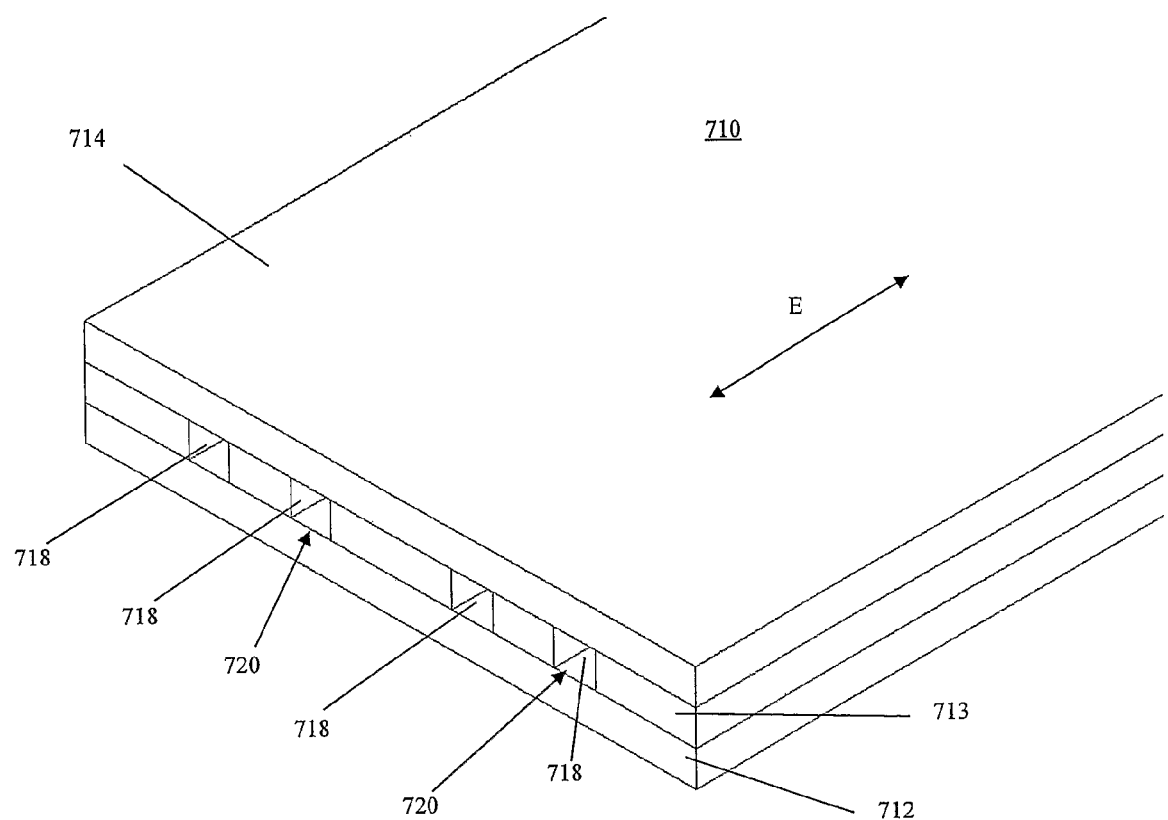
FIG. 22 is a cross sectional axonometric view of a lead in accordance with an eighth embodiment of the present invention.

FIG. 22 shows a cross sectional axonometric view of a lead 710 in accordance with an eighth embodiment. The lead 710 is elongate in the direction indicated by double-headed arrow E. Accordingly, the lead 710 as viewed in FIG. 21 has been sectioned in a direction transverse to the elongate direction E of the lead 710.

As shown in FIG. 22, the lead 710 has a first stratum 712 that is elongate and generally flat, such that the first stratum 712 has a generally ribbon-like shape. The lead 710 further has a second stratum 713 and a third stratum 714 that are both also of generally ribbon-like shape. The first stratum 712 is affixed to the second stratum 713. Similarly, the second stratum 713 is affixed to the third stratum 714 such that the lead 710, in this embodiment, also has a generally ribbon-like shape.

In this embodiment, the second stratum 713 is provided with a plurality of channels 718, which are cut, or otherwise formed such that each channel 718 extends through the thickness of the second stratum 713. Conduits 720 that are each bounded by the first stratum 712, the second stratum 713 and the third stratum 714 extend in the elongate direction within the lead 710.

The lead 710 may be connected to a sensor in any desired manner, for example, such as described in connection with the lead 510. Particularly, the lead 710 can be readily connected to a sensor of laminate construction by laminating the first, second and third strata 712, 713, 714 within the laminate structure of the sensor. For example, an end portion of the lead 710, having conduits 720 that open onto an end face of the lead 710, can be affixed to one or more strata of the sensor.

FIGS. 23a to 23d respectively show schematically a base stratum 212' and a terminal stratum 214' of a sensor 210' in accordance with a ninth embodiment.

FIG. 23a shows a bottom view of the base stratum 212' has a plurality of first channel portions 218', each of which extends partially through the thickness of the base stratum 212' and opens onto the bottom surface of the base stratum 212'. The base stratum 212 further has a plurality of second channel portions 220', each of which also extends partially through the thickness of the base stratum 212' and opens onto the bottom surface of the base stratum 212'. In this embodiment, each of the first channel portions 218' is longer than the second channel portions 220' such that the ends of the first channel portions 218' extend beyond the ends of the second channel portions 220'. In use, the bottom surface of the base stratum 212' is affixed to the surface of a component.

The opposite, top surface of the base stratum 212' is shown in FIG. 23b. The top surface has a plurality of first hole portions 238' that extend partially through the thickness of the base stratum 212' and open onto the top surface of the base stratum 212'. Each of the first hole portions 238' also opens into, and is in fluid communication with, an end of one of the second channel portions 220'. Accordingly, in this embodiment the second channel portions 220' and first hole portions 238' together form second channels in the base stratum 212' that extend through the thickness of the base stratum 212'.

In addition, the top surface of the base stratum 212' is provided with a plurality of second hole portions 240a' and a plurality of channel portions 240b' that each extend partially through the thickness of the base stratum 212'; the second hole portions 240a' and channel portions 240b' open onto the top surface of the base stratum 212'. The second hole portions 240a' open into, and are in fluid communication with, one end of one of the first channel portions 218'. The channel portions 240b' are elongate, and opens into, and is in fluid communication with, the ends of two adjacent first channel portions 218' such that the respective two first channel portions 218' are in fluid communication via one of the channel portions 240b'.

Accordingly, the first channel portions 218', the second hole portions 240a' and channel portions 240b' together form first channels in the base stratum 212' that extend through the thickness of the base stratum 212'.

The bottom surface of the terminal stratum 214' (which is shown in FIG. 23c) is affixed to the top surface of the base stratum 212'. The bottom surface of the terminal stratum 214' has a plurality of first hole portions 242' that extend partially through the thickness of the terminal stratum 214' and open onto the bottom surface of the terminal stratum 214'. Each of the first hole portions 242' registers with one of the second holes 240a' in the top surface of the base stratum 212'.

In addition, the bottom surface of the terminal stratum 214' has a plurality of channel portions 244' that each extend partially through the thickness of the terminal stratum 214' and open onto the bottom surface of the terminal stratum 214'. The channel portions 244' are elongate, and each registers with two adjacent first hole portions 238' in the top surface of the base stratum 212' such that the respective two first hole portions 238' are in fluid communication via one of the channel portions 244b'.

As shown in both FIGS. 23c and 23d, the terminal stratum 214' is provided with first holes 242' that each extend through the terminal stratum 214' and register with one the second hole portions 240a' in the top surface of the base stratum 212'. The terminal stratum 214' is further provided with has second holes 248' that each extend through the terminal stratum 214' and register with one the first hole portions 238' in the top surface of the base stratum 212'.

For clarity connectors to connect the sensor 210' into a differential pressure monitoring system have been omitted.

FIG. 24 shows schematically the sensor 210' in plan view, in which each of the base stratum 212' and the terminal stratum 214' have been illustrated in transparent form for clarity. FIG. 24a shows a cross sectional view of the sensor 210' as viewed along the line B'-B' in FIG. 24. FIG. 24b shows a cross sectional view of the sensor 210' as viewed along the line C'-C' in FIG. 24.

A first conduit 226' is formed by the first channels in the base stratum 212' and the first holes 242' in the terminal stratum 214'. Similarly, a second conduit 228' is formed by the second channels in the base stratum 212', and the channel portions 244b' and second holes 248' in the terminal stratum 214'.

It will be understood to persons skilled in the art of the invention that many modifications may be made without departing from the scope of the invention. For example, each stratum of the sensor and/or lead may be formed of a structural adhesive, which can be cured by the application of heat. In an embodiment of the sensor having strata of structural adhesive the structural adhesive may additionally be provided with a pressure sensitive adhesive (PSA) dispersed within the formulation. The PSA allows the sensor to be removed and repositioned prior to the structural adhesive of the sensor being cured. Similarly, the PSA allows the strata within the sensor to be weakly affixed to one another prior to curing of the structural adhesive. In embodiments of the sensor in which strata are made of plastics or metal alloys, the use of a structural adhesive containing dispersed PSA can assist affixing of one stratum to another, or the sensor to the component to be monitored.

In one embodiment, the various strata within the sensor or lead may be affixed to one another by diffusion bonding of adjacent strata. Similarly, the affixing of a lead to, or within, a sensor may be achieved using diffusion bonding.

It is to be appreciated that the choice of materials used in embodiments of sensors in accordance with the present invention is not essential. The requirements of the particular application and environment in which a sensor is used will influence the selection of material(s).

It is to be appreciated that there are a number of alternative methods for affixing one stratum to an adjacent stratum, or similarly affixing a connector to an adjacent stratum, and affixing a lead to a sensor. For example, adhesion using adhesives and/or sealants may be employed. Alternatively, in embodiments in which the strata are made of plastics materials, plastic welding (either direct or indirect) may be employed. Alternatively, a bond may be formed using a heat or pressure, or a combination of both. In a further alternative, a solvent product may be delivered to one or both of the surfaces of the strata to be affixed. Upon contact between the strata the solvent product can fuse the two strata together. In a further alternative, diffusion bonding may be employed. It is to be further appreciated that one or more of the above methods may be employed to form a sensor according to an embodiment of the present invention. In addition, it is to be appreciated that any of the above methods may be employed to affix the base stratum of a sensor to a surface of a component.

It is to be appreciated that the connector(s) may be of any desired shape and structure, provided that the connectors fulfill the function of connecting the conduit(s) within the sensor to the tubing that plumbs the sensor into the monitoring system. Furthermore, the connection(s) should also form a substantial hermetic seal.

In one embodiment, connectors can be affixed to the respective strata by an interference fit. In one alternative, the connector may be provided with an external screw thread that engages a complementary thread in the respective strata.

In an alternative embodiment, the tubing to plumb the sensor into the monitoring system may be affixed directly to the body portion. Accordingly, in such an alternative embodiment the connector may be omitted.

In this specification, it will be appreciated that the term "fluid" may mean either liquid or gas. However, it will be appreciated that gas is the preferred fluid in a differential pressure monitoring system.

Furthermore, it will be appreciated that in a sensor of the present invention the dimensions of the channels will influence the sensitivity of the monitoring system. In addition, the actual separation of the channels in the base stratum will also influence the sensitivity of the monitoring system. In some embodiments, such as that illustrated in FIGS. 1 to 6a, the separation of adjacent channels is less than, or equal to, the width of the channels.

However, in some applications embodiments may be provided that have varied separation of adjacent channels in the base stratum and/or channels in the base stratum of non-uniform width along their length.

In some embodiments, a plurality of channels may be provided in the base stratum that are connected by holes/channels in intermediate strata and/or terminal strata, such that the sensor has a single conduit that extends through the sensor.

In some embodiments, a channel in a stratum of the sensor may be in the form of one or more first portions that extend partially through the thickness of the stratum and open onto a first surface of the respective stratum, and one or more second portions that extend partially through the thickness of the stratum and open onto a second opposing surface of the respective stratum, with the first and second portions being in fluid communication with one another. Accordingly, the channel as a whole extends through the thickness of the respective stratum.

In the claims of this application and in the description of the invention, except where the context requires otherwise due to express language or necessary implication, the words "comprise" or variations such as "comprises" or "comprising" are used in an inclusive sense, i.e. to specify the presence of the stated features but not to preclude the presence or addition of further features in various embodiments of the invention.

The invention claimed is:

1. A sensor for detecting the presence of a surface crack in a component, the sensor comprising:
    a base stratum that, in use, is affixed to the surface of the component, the base stratum having one or more channels each of which extends through the thickness of the base stratum, and
    a terminal stratum that is affixed to the base stratum, the terminal stratum having at least one hole each of which extends through the thickness of the terminal stratum and registers with the one or more of the channels to form one or more conduits that extend through the sensor.

2. A sensor as claimed in claim 1, wherein the base stratum is provided with a plurality of channels.

3. A sensor as claimed in claim 2, wherein the one or more conduits comprise a plurality of channels that each extend through the sensor, and wherein, when the sensor is affixed to the component and the component is intact, the conduits are in fluid isolation from each other.

4. A sensor as claimed in claim 2, wherein adjacent ones of the plurality of channels are separated by a distance equal to or less than a width of the channels.

5. A sensor as claimed in claim 1, further comprising a connector attached to the terminal stratum, the connector having one or more tubes each register with respective ones of the holes in the terminal stratum.

6. A sensor as claimed in claim 5, wherein the connector further comprises a flanged portion that surrounds one or more of the tubes, the flanged portion being affixed to the terminal stratum.

7. A sensor as claimed in claim 6, wherein the flanged portion is attached to the terminal stratum by an adhesive.

8. A sensor as claimed in claim 7, wherein the base stratum is affixed to the surface of the component by an adhesive, the adhesive further providing a seal between the base stratum and the surface.

9. A sensor as claimed in claim 8, wherein the sensor is provided with a release layer for protecting the adhesive on the base stratum prior to attachment to the surface.

10. A sensor as claimed in claim 7, wherein the adhesive is a pressure sensitive adhesive.

11. A sensor as claimed in claim 1, wherein each of the base and terminal stratum comprises a film.

12. A sensor as claimed in claim 10, wherein the terminal stratum further comprises an adhesive for affixing the terminal stratum to the base stratum and establishing a seal at the interface therebetween.

13. A sensor for detecting the presence of a surface crack in a component, the sensor comprising:
    a base stratum that, in use, is affixed to the surface of the component, the base stratum having one or more channels that each extend through the thickness of the base stratum;
    at least one intermediate stratum that is affixed to two adjacent strata and has one or more holes and/or channels that each extend through the thickness of the intermediate stratum, each hole/channel registering with one or more of the holes/channels in an adjacent stratum;
    a terminal stratum that is affixed to an adjacent one of the intermediate stratum, the terminal stratum having at least one hole each of which extends through the thickness of the terminal stratum and registers with the one or more of the holes/channels in the adjacent intermediate stratum; and one or more conduits that extend through the sensor, the conduits being formed by the registering holes/channels in the:
base stratum,
the at least one intermediate stratum; and,
the terminal stratum.

14. A sensor as claimed in claim 13, wherein the base stratum is provided with a plurality of channels.

15. A sensor as claimed in claim 14, wherein adjacent ones of the plurality of channels are separated by a distance equal to or less than a width of the channels.

16. A sensor as claimed in claim 13, wherein the one or more conduits comprises a plurality of channels that each extend through the sensor, and wherein, when the sensor is affixed to the component and the component is intact, the conduits are in fluid isolation from each other.

17. A sensor as claimed in claim 13, further comprising a connector attached to the terminal stratum, the connector having one or more tubes that register with respective ones of the holes in the terminal stratum.

18. A sensor as claimed in claim 17, wherein the connector further comprises a flanged portion that surrounds one or more of the tubes, the flanged portion being affixed to the terminal stratum.

19. A sensor as claimed in claim 18, wherein the flanged portion is attached to the terminal stratum by an adhesive.

20. A sensor as claimed in claim 19, wherein the adhesive is a pressure sensitive adhesive.

21. A sensor as claimed in claim 13, wherein the base stratum is affixed to the surface of the component by an adhesive, the adhesive further providing a seal between the base stratum and the surface of the component.

22. A sensor as claimed in claim 21, wherein the sensor is provided with a release layer for protecting the adhesive on the base stratum prior to affixing the sensor to the surface of the component.

23. A sensor as claimed in claim 21, wherein each of the at least one intermediate stratum and the terminal stratum further comprises an adhesive for affixing the respective stratum to an adjacent stratum and establishing a seal at the interface therebetween.

24. A sensor as claimed in claim 13, wherein each of the base stratum, the at least one intermediate stratum and the terminal stratum comprises a film.

25. A sensor for detecting the presence of a surface crack in a component, the sensor comprising:
a base stratum that, in use, is affixed to the surface of the component, the base stratum having one or more channels that each extend through the thickness of the base stratum;
at least one intermediate stratum that is affixed to two adjacent strata and has one or more holes and/or channels that each extend through the thickness of the intermediate stratum, each hole/channel registering with one or more of the holes/channels in an adjacent stratum;
a terminal stratum that is affixed to the adjacent intermediate stratum;
one or more first conduits that extend through the sensor, the first conduits being formed by the holes/channels in the base stratum and the at least one intermediate stratum; and
an elongate lead that has a first stratum and a second stratum and one or more second conduits that extend in the elongate direction through the lead, each of the second conduits being in fluid communication with one of the first conduits.

26. A sensor as claimed in claim 25, wherein the second stratum is affixed to the first stratum, and at least one of the first and second strata is provided with one or more channels that extend partially through the thickness of the respective first and second strata and form the second conduits.

27. A sensor as claimed in claim 26, wherein both the first and second strata are provided with channels that extend partially through the thickness of the respective first and second strata and form the second conduits.

28. A sensor as claimed in claim 27, wherein the channels in the first stratum register with the channels in the second stratum, such that pairs of channels in the first and second strata that register together form one of the second conduits.

29. A sensor as claimed in claim 26, wherein an end portion of the lead is affixed to at least one of the base stratum, at least one intermediate stratum and terminal stratum.

30. A sensor as claimed in claim 29, wherein the end portion of the lead is affixed to at least two of the base stratum, at least one intermediate stratum and terminal stratum.

31. A sensor as claimed in claim 29, wherein the terminal stratum has one or more holes or channels that each form a portion of the first conduits, and the end portion of the lead is affixed to the terminal stratum.

32. A sensor as claimed in claim 31, wherein the each of the second conduits opens onto the end portion of the lead such that each of the second conduits registers with one of the holes or channels in the terminal stratum.

33. A sensor as claimed in claim 26, wherein the base stratum is provided with a plurality of channels.

34. A sensor as claimed in claim 33, wherein the one or more first conduits comprises a plurality of first conduits that each extend through the sensor, and wherein, when the base stratum is affixed to the component and the component is intact, each of the first conduits is in fluid isolation from the other first conduits.

35. A sensor as claimed in either claim 33, wherein adjacent ones of the plurality of channels are separated by a distance which is equal to or less than a width of the channels.

36. A sensor as claimed in claim 26, further comprising a connector attached to the terminal stratum, the connector having one or more tubes that each register with one of the at least one hole in the terminal stratum.

37. A sensor as claimed in claim 36, wherein each of the tubes is extends through an opening in an end portion of the lead and into one of the second conduits.

38. A sensor as claimed in claim 36, wherein the connector further comprises a flanged portion that surrounds one or more of the tubes, the flanged portion being affixed to the terminal stratum.

39. A sensor as claimed in claim 38, wherein the flanged portion is attached to the terminal stratum by an adhesive.

40. A sensor as claimed in claim 26, wherein the base stratum is affixed to the surface of the component by an adhesive, the adhesive further providing a seal between the base stratum and the surface of the component.

41. A sensor as claimed in claim 40, wherein the sensor is provided with a release layer for protecting the adhesive on the base stratum prior to affixing the sensor to the surface of the component.

42. A sensor as claimed in claim 41, wherein the adhesive is a pressure sensitive adhesive.

43. A sensor as claimed in claim 26, wherein each of the strata comprises a film.

44. A sensor as claimed in claim 43, wherein each of the at least one intermediate stratum and the terminal stratum further comprises an adhesive for affixing the respective stratum to an adjacent stratum and establishing a seal at the interface therebetween.

45. A sensor as claimed in claim 43, wherein each of the first and second strata further comprise an adhesive for affixing the respective first and second strata to the adjacent strata and establishing a seal at the interface therebetween.

46. A sensor as claimed in claim 25, wherein the lead further has an intermediate lead stratum to which each of the first and second strata are affixed, the intermediate lead stratum having one or more cuts that each extend through the thickness of the intermediate strata and form one of the second conduits.

* * * * *